(12) United States Patent
Brady et al.

(10) Patent No.: US 7,002,679 B2
(45) Date of Patent: Feb. 21, 2006

(54) ENCODED EXCITATION SOURCE RAMAN SPECTROSCOPY METHODS AND SYSTEMS

(75) Inventors: David J. Brady, Durham, NC (US); Nikos P. Pitsianis, Durham, NC (US); Zhaochun Xu, Durham, NC (US)

(73) Assignee: Duke University, Durham, NC (US)

( * ) Notice: Subject to any disclaimer, the term of this patent is extended or adjusted under 35 U.S.C. 154(b) by 65 days.

(21) Appl. No.: 10/843,123

(22) Filed: May 11, 2004

(65) Prior Publication Data

US 2005/0254047 A1   Nov. 17, 2005

(51) Int. Cl.
*G01J 3/44* (2006.01)
*G01N 21/65* (2006.01)

(52) U.S. Cl. .................................................... 356/301
(58) Field of Classification Search ................. 356/301
See application file for complete search history.

(56) References Cited

U.S. PATENT DOCUMENTS

| | | | |
|---|---|---|---|
| 5,257,086 A | 10/1993 | Fateley et al. | |
| 5,455,673 A | 10/1995 | Alsmeyer et al. | |
| 2002/0057431 A1 * | 5/2002 | Fateley | 356/330 |
| 2002/0171834 A1 | 11/2002 | Rowe et al. | |

* cited by examiner

*Primary Examiner*—F. L. Evans
(74) *Attorney, Agent, or Firm*—Myers Bigel Sibley & Sajovec (57) ABSTRACT

Selected combinations from three or more light excitation wavelengths are serially impinged on a sample based on an encoding pattern. A plurality of spectra is detected from the sample responsive to respective ones of the selected combinations of light excitation wavelengths. A shifted Raman excitation spectral component and a non-shifted spectral component characteristic of the sample are identified based on the plurality of spectra.

31 Claims, 9 Drawing Sheets

ENCODED EXCITATION SOURCE RAMAN SPECTROSCOPY METHODS AND SYSTEMS

STATEMENT OF GOVERNMENT SUPPORT

This invention was made with Government support under grant number NO1AA23013 from the National Institutes on Alcoholism and Alcohol Abuse. The Government has certain rights to this invention.

BACKGROUND OF THE INVENTION

The present invention relates to methods and systems for spectroscopy, and more particularly, to Raman Spectroscopy.

The wavelength of light scattered inelastically from molecular species can be shifted due to energy coupling to the internal vibrational modes of the scattering species. Such frequency shifts may result in a discrete array of sharp lines corresponding to harmonic modes of the molecule. This spectral shift is generally referred to as the "Stokes" shift or the "Raman" effect. Raman spectroscopy may be used to identify the presence of a target molecule, to analyze the structure and/or densities of molecular species, and/or for other purposes. However, fluorescence produced by elastic scattering and/or stray light may obscure the Raman portion of the spectrum.

Shifted Excitation Raman Difference Spectroscopy ("SERDS") may be used to reduce interference from fluorescence and stray light by shifting the frequency of a laser light that is impinged on a specimen. The Raman bands are generally shifted in response to a shift in excitation frequency, and the broad background fluorescence and stray light are generally much less affected by the excitation frequency shift. SERDS generally involves a subtraction of two spectra obtained from two different (shifted) excitation frequencies. The subtraction can result in a derivative spectrum that may reduce the background and fluorescence spectra. See S. E. J. Bell, E. S. O. Bourguignon, and A. Dennis, "Analysis of luminescent samples using subtracted shifted raman spectroscopy," *Analyst*, vol. 123, no. 8, 1729–1734 (1998); P. Matousek, M. Towrie, and A. W. Parker, "Fluorescence background suppression in raman spectroscopy using combined kerr gated and shifted excitation raman difference techniques," *Journal of Raman Spectroscopy*, vol. 33, no. 4, 238–242 (2002); A. P. Shreve, N. J. Cherepy, and R. A. Mathies, "Effective rejection of fluorescence interference in raman-spectroscopy using a shifted excitation difference technique," *Applied Spectrocopy*, vol. 46, no. 4, 707–711 (1992); J. Zhao, M. M. Carrabba, and F. S. Allen, "Automated fluorescence rejection using shifted excitation raman difference spectroscopy," *Applied Spectroscopy*, vol. 56, no. 7,934–945 (2002).

However, SERDS may not sufficiently reduce fluorescence and stray light in all environments. For example, Raman spectroscopy may be more difficult in diffuse media, such as biological tissue, because the Raman effect may be obscured by a high level of incoherent fluorescence spectra and/or by the diversity of molecules and the associated Raman signals that may be present in the media. Raman spectra may also be difficult to isolate in diffuse media because of the spatial incoherence of the scattered signal.

SUMMARY OF EMBODIMENTS OF THE INVENTION

According to embodiments of the present invention, selected combinations from three or more light excitation wavelengths are serially impinged on a sample based on an encoding pattern. A plurality of spectra is detected from the sample responsive to the selected combinations of light excitation wavelengths. A shifted Raman excitation spectral component and a non-shifted spectral component characteristic of the sample are identified based on the plurality of spectra.

In some embodiments, the selected combinations are multi-wavelength light excitation beams. Identifying a shifted Raman excitation spectral component and a non-shifted spectral component can include comparing ones of the plurality of spectra and identifying components of the spectra that are shifted or non-shifted responsive to changes in wavelengths of the selected combinations. The encoding pattern can include a at least a portion of Hadamard encoding pattern and/or a Walsh encoding pattern.

In particular embodiments, selectively impinging selected combinations from three or more light excitation wavelengths can include selectively illuminating radiation source elements in an array of radiation source elements according to the encoding pattern. A first subset and a second subset of non-overlapping radiation source elements can be identified from the array of radiation source elements. The selected combinations can include a first excitation beam including the first subset of radiation source elements and a second excitation beam including the second subset of radiation source elements. A shifted Raman excitation spectral component and a non-shifted spectral component can by identified by determining a difference between a spectrum responsive to the first excitation beam and a spectrum responsive to the second excitation beam. The first subset and the second subset of radiation source elements can include the same number of radiation source elements. The first subset and the second subset of radiation source elements can be selected based on at least a portion of a Hadamard encoding pattern. The first subset of radiation source elements can be based on a row or column of a Hadamard matrix and the second subset of radiation source elements can be based on an inverse of the row or column of the Hadamard matrix. A shifted Raman excitation spectral component and a non-shifted spectral component can be identified by analyzing the plurality of spectra using a Hadamard encoding pattern.

In some embodiments, the non-shifted spectral component includes fluorescence radiation. The radiation source elements can include light diodes and/or lasers. The multi-wavelength light excitation beams can include three or more wavelengths. In further embodiments, selected combinations from three or more light excitation wavelengths can be serially impinged on the sample by filtering a broadband excitation source to provide the selected wavelength combination.

According to further embodiments of the invention, systems for performing Raman spectroscopy are provided. An electromagnetic radiation source is configured to serially impinge selected combinations from three or more light excitation wavelengths on a sample based on an encoding pattern. A detector is configured to detect a plurality of spectra from the sample responsive to respective ones of the selected combinations. A signal analyzer is in communication with the detector and configured to receive the plurality of spectra and to identify a shifted Raman excitation spectral component and a non-shifted spectral component characteristic of the sample based on the plurality of spectra.

DETAILED DESCRIPTION OF EMBODIMENTS OF THE INVENTION

The present invention now will be described more fully hereinafter with reference to the accompanying drawings, in which various embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the relative sizes of elements may be exaggerated for clarity. Like reference numerals in the drawings denote like members.

When an element is described as being "on" or "adjacent to" another element, the element may be directly on the other element, or other elements may be interposed therebetween. In contrast, when an element is referred to as being "directly on" another element, there are no intervening elements present. The thicknesses of elements or regions may be exaggerated for clarity.

Figure 1:
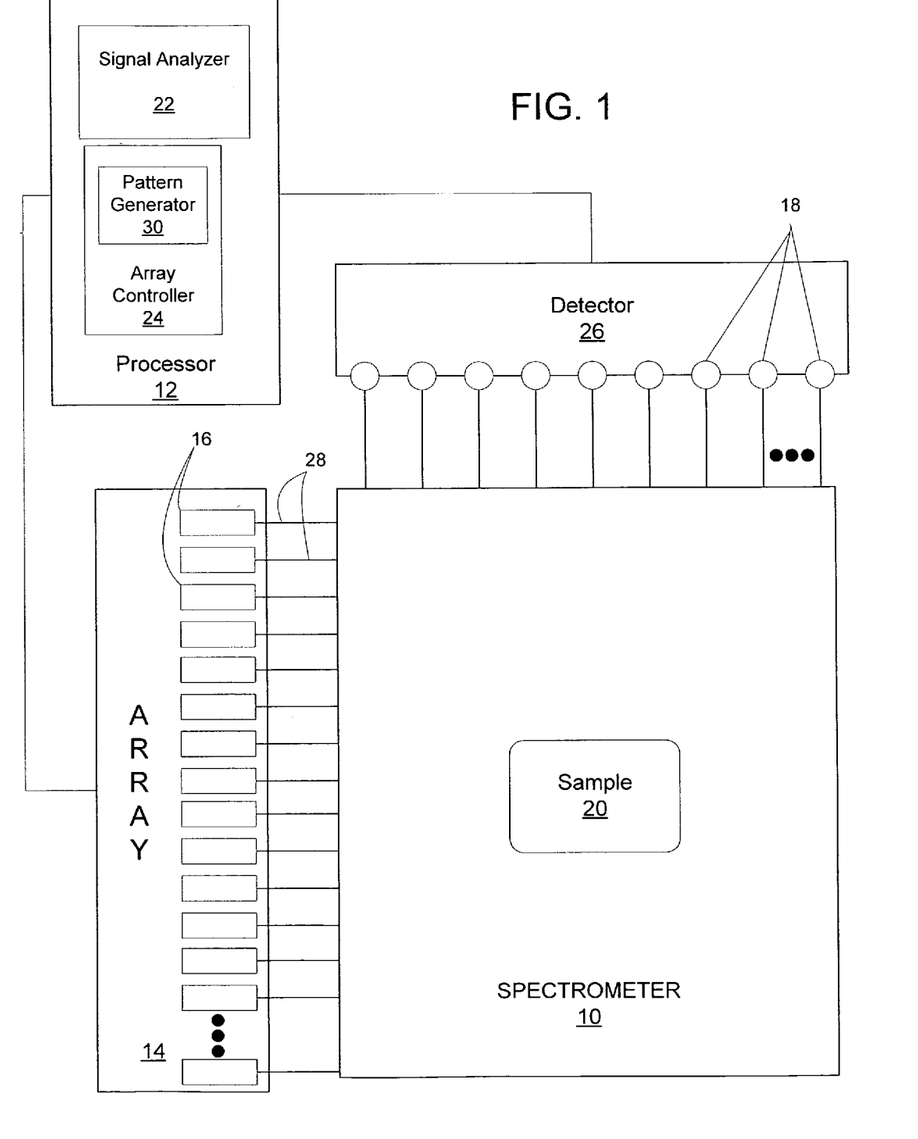
FIG. 1 is a schematic diagram of Raman spectroscopy systems and methods according to embodiments of the present invention including an excitation array.

As illustrated in FIG. 1, a sample 20 is placed in a Raman spectrometer 10. A plurality of radiation source elements 16 from an excitation beam array 14 configured to impinge an excitation beam(s) on the sample 20 in the spectrometer 10. The radiation source elements 16 are connected to the spectrometer 10 by at least three inputs 28, which provide the excitation beam(s) to the sample 20. When an excitation beam is impinged on the sample 20, the resulting re-emitted light is detected by a plurality of detectors 18 in a detector array 26. The detector 26 and the excitation beam array 14 are in communication with a processor 12. The processor includes a signal analyzer 22 and an array controller 24.

The array controller 24 includes a pattern generator 30, which can be configured to select a combination from three or more light excitation wavelengths from the excitation beam array 14 based on an encoding pattern. The excitation beam typically includes multi-wavelength light. For example, various encoding patterns can be used to serially select a combination of some or all of the radiation source elements 16. The array controller 24 delivers control signals to the excitation beam array 14 to illuminate selected ones of the radiation source elements 16. The pattern generator 30 can use at least a portion of a Hadamard or Walsh encoding pattern to select a series of excitation beams. For example, one or more rows or columns of a Hadamard or Walsh matrix can be used to select excitation beams in a series of excitation beams.

The resulting re-emitted light from the sample 20 is detected by the detector array 26 as spectra that are responsive to combinations of light excitation wavelengths from the excitation beam array 14. The spectra can be received by the processor 12 and analyzed by the signal analyzer 22. For example, the signal analyzer 22 can identify a shifted Raman excitation spectral component and a non-shifted spectral component characteristic of the sample 20 based on the detected spectra.

In this configuration, multi-wavelength light excitation beams can be used to obtain spectra from the sample 20. The excitation beams are selected combinations from three or more light excitation wavelengths. For example, if the excitation beams are selected from three light excitation wavelengths, the resulting excitation beams can include any combination of one, two, or all three of the light excitation wavelengths. The shifted Raman excitation spectral component and the non-shifted spectral component can be isolated, for example, by comparing the detected spectra and identifying components of the spectra that are shifted and/or non-shifted responsive to changes in wavelengths of the selected wavelength combinations. Thus, the non-Raman components of the spectrum, such as fluorescence and stray light, may be reduced and/or the signal-to-noise ration can be improved.

Without wishing to be bound by theory, the spectrum of scattered light from the sample 20 generally contains both Raman and non-Raman components. The non-Raman components are primarily fluorescence signals. The Raman components generally differ from the non-Raman components in that the frequencies of the fluorescence signals are determined by the nature of the scattering molecules in the sample 20. On the other hand, the frequencies of the Raman components are determined both by the nature of the molecules and by the spectrum of the excitation light beam. As a result, the Raman spectral components may shift based on the wavelength(s) of the excitation light beam. In contrast, the non-Raman components may be relatively stable regardless of the wavelength(s) of the excitation beam. Therefore, the Raman components and the non-Raman components of the spectra can be isolated based on the frequency shift observed in the Raman spectral components. For example, two or more spectra can be detected by the detector array 26 responsive to different combinations of excitation wavelengths. The difference between the spectra can be determined to isolate the constant components of the spectra (e.g., non-Raman components that do not shift due to changes in excitation wavelengths) and shifted Raman components of the spectra.

In some embodiments, the radiation source elements 16 are narrow bandwidth light sources, Such as light emitting diodes or lasers having a bandwidth of about one-fourth of a nanometer. Combinations of wavelengths selected from three or more wavelengths can be impinged on the sample 20 by selectively illuminating the radiation source elements 16 according to the encoding pattern. In particular embodiments, the encoding pattern can include subsets of non-overlapping radiation source elements 16 from the array 14. Excitation beams corresponding to each subset can be impinged on the sample 20. The difference between the resulting spectra from each subset can be determined to identify a shifted Raman excitation spectral component and/or a non-shifted spectral component. The subsets of selected radiation source elements can include the same number of radiation source elements and may be based on a Hadamard encoding pattern. For example, one subset of radiation source elements can be based on a row or column of a Hadamard matrix and another subset can be based on the inverse of the same row or column of the Hadamard matrix.

Although the array 14 of radiation source elements 16 is illustrated in FIG. 1, it should be understood that various types of excitation sources can be used according to embodiments of the invention to provide encoded combinations of wavelengths. For example, as illustrated by the spectrometer 110 of FIG. 2, a broadband excitation source 114 and a filter 116 can be used to impinge selected wavelengths from the broadband excitation source 114 on a sample 120. The resulting re-emitted light is detected by a detector 126. The broadband source 114, the filter 116 and the detector 126 are in communication with a processor 112. The broadband source 114 can be a superluminescent light emitting diode, a white light source, and/or a multimode diode. As used herein, "broadband" refers to any bandwidth that is sufficiently broad so that it can be filtered to provide more than one narrow bandwidth excitation beam.

Figure 2:
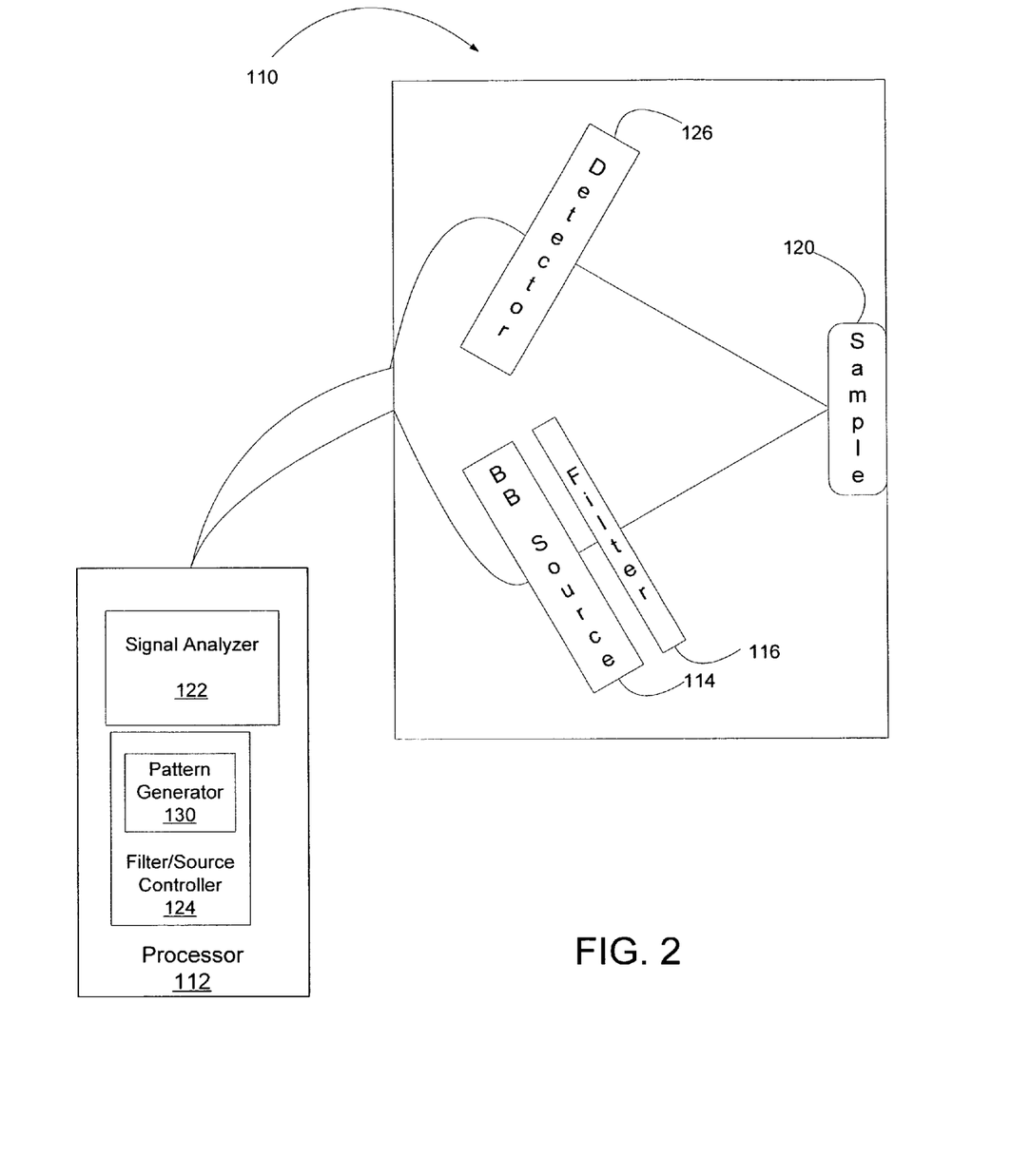
FIG. 2 is a schematic diagram of Raman spectroscopy systems according to further embodiments of the present invention including a broadband excitation source.

The processor 112 can include components similar to the processor 12 illustrated in FIG. 1, such as a signal analyzer 112. The processor 112 also includes a filter/source controller 124 for controlling the wavelength combinations that are selectively impinged on the sample. The filter/source controller 124 can include a pattern generator 130 for generating patterns of wavelength combinations, such as Hadamard encoding patterns. For example, the filter/source controller 124 can communicate instructions to the spectrometer 110 to shine the broadband source 114 through a series of filters, including the filter 116 as illustrated, e.g., by moving various filters in front of the broadband source 114 or by moving the broadband source 114 such that the excitation beam passes through the desired filter. The series of filters can be selected to provide the selected combinations of wavelengths based on the encoding pattern generated by the pattern generator 130. Alternatively, a user can manually select an appropriate filter and pass the broadband excitation beam through the selected filter. The pattern generator 130 can provide the a list of filters based on an encoding pattern.

In particular embodiments, the detectors 26, 126 are multiplex detector arrangements, such as may be used in a Hadamard spectrometer. A Hadamard spectrometer is a multiplexing spectrometer that uses the optical components of a dispersive spectrometer with a Hadamard encoding mask.

Although FIGS. 1 and 2 are illustrated, for example, with respect to the spectrometers 10, 110, processors 12, 112, respectively, as well as specific configurations of detectors 26, 126 and light sources, i.e., the array 14 and broadband source 114, respectively, the present invention should not be construed as limited to the configurations shown in FIGS. 1 and 2, but is intended to encompass any configuration capable of carrying out the operations described herein. In some embodiments, the components illustrated in FIGS. 1 and 2 can be incorporated into other components. For example, the array 14 and/or the detector 26 in FIG. 1 can be incorporated into the spectrometer 10. The array 14 of FIG. 1 and the broadband source 114 and filter 116 of FIG. 2 may be used interchangeably. The broadband source 114, filter 116 and/or detector 126 in FIG. 2 can be provided as separate components from the spectrometer 110. In addition, the respective signal analyzers 22, 122, pattern generators 30, 130, and processors 12, 112 as well as the array controller 24 and/or filter source controller 124 can be incorporated into other components, such as the respective spectrometers 10, 110.

Figure 3:
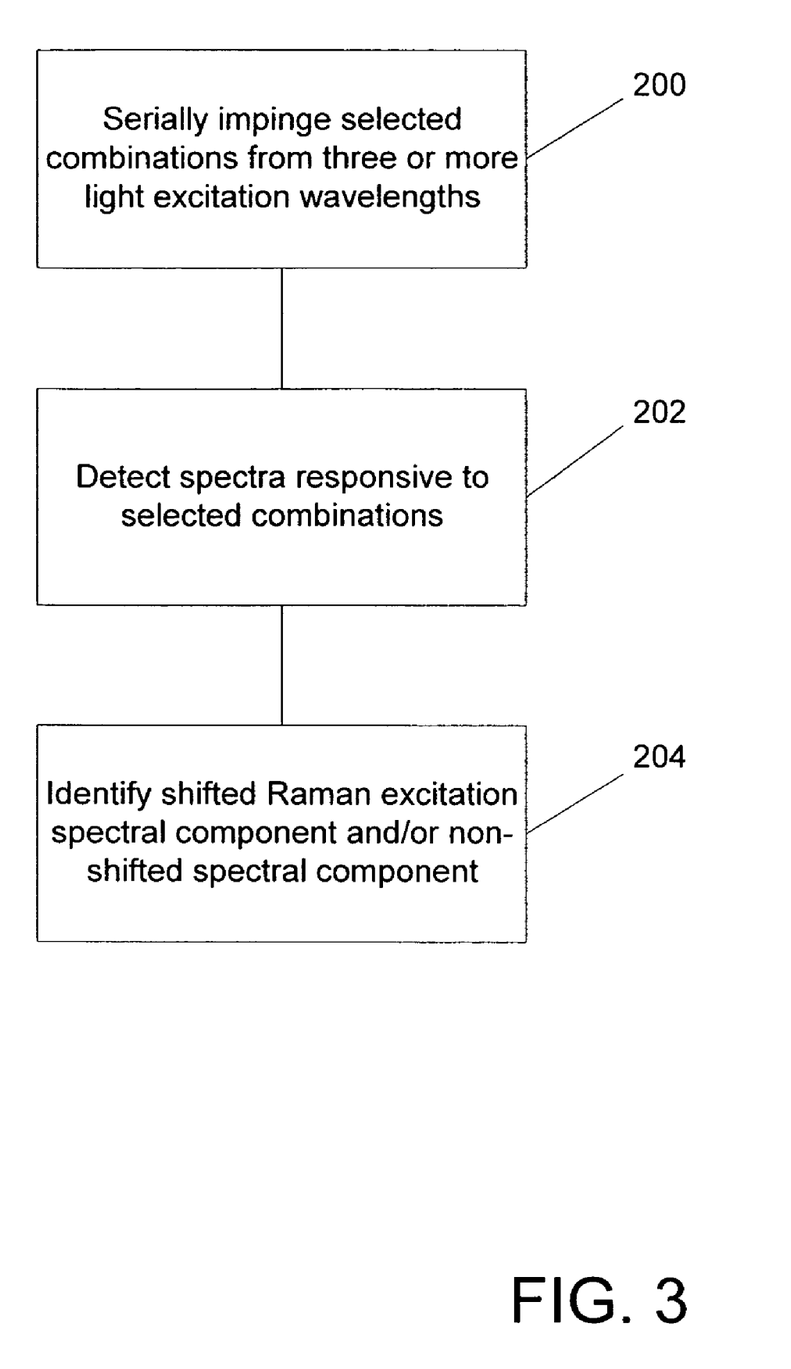
FIG. 3 is a flowchart illustrating operations according to embodiments of the present invention.

As shown in FIG. 3, operations according to embodiments of the present invention can include serially impinging selected combinations from three or more light excitation wavelengths on a sample based on an encoding pattern (Block 200). The light excitation wavelengths can be selected from three or more light excitation wavelengths. Multi-wavelength excitation beams can be used. As discussed with respect to FIGS. 1 and 2, the light excitation wavelengths can be provided by an array of narrow bandwidth excitation sources, such as excitation sources 16 in the array 14 of FIG. 1, and/or by a broadband excitation source and filter arrangement, such as the broadband source 114 and filter 116 of FIG. 2. The wavelengths of the light sources can be selected to excite molecules in the source to re-emit a Raman excitation spectrum. Spectra from the sample that are responsive to the selected combinations of light excitation wavelengths can be detected (Block 202), such as by detectors 26, 14 in FIGS. 1 and 2, respectively. A shifted Raman excitation spectral component and/or a non-shifted spectral component characteristic of the sample can be identified based on the plurality of spectra (Block 204).

Embodiments of the present invention will now be described with respect to the following non-limiting examples.

EXAMPLE 1

Raman Molecular Response Calculation

A spectral impulse response can be used to make a mathematical distinction between a non-Raman signal (e.g., the component of a spectrum that can be attributed to non-Raman scattering) and the Raman signal (e.g., the component of a spectrum that can be attributed to Raman scattering). Both spectral components may include sub-components that are linear and non-linear with respect to the exciting wavelengths. However, the linear components are generally stronger than the non-linear components. The linear terms can be described by an impulse response. The non-Raman spectrum, $S_{NR}$, generated by a linear transformation of the exciting intensity can be expressed as follows:

$$S_{NR}(\nu,t) = \int h_{NR}(\nu,\nu') S_e(\nu',t) d\nu' \tag{1}$$

where $S_e(\nu, t)$ is the exciting signal as a function of optical output frequency $\nu$ and the slow time t; $h_{NR}$ is the non-Raman impulse response and $\nu'$ is an exciting frequency. The distinguishing feature of the Raman and the non-Raman signals is that the Raman impulse response is typically shift invariant in the exciting field, while the non-Raman impulse response is not shift invariant. The term "shift invariant" means that the Raman impulse response is a function only of the difference between the observed frequency and the exciting frequency, e.g., $h_R(\nu,\nu') = h_R(\nu-\nu')$. Therefore, the Raman spectrum can be expressed as follows:

$$S_R(\nu,t) = \int h_R(\nu-\nu') S_e(\nu',t) d\nu' \tag{2}$$

The total inelastic scattered spectrum from a source is the sum of the non-Raman and the Raman terms.

$$S_T(\nu,t) = S_{NR}(\nu,t) + S_R(\nu,t) \tag{3}$$

EXAMPLE 2

Raman Signal Discrimination Using Coded Illumination

The structural difference between the Raman and non-Raman impulse responses described in Example 1 can be used to isolate the signals from each other. Specifically, the Raman impulse response can be determined from measurements of the total spectrum. To achieve this, the excitation signal is temporally and spectrally encoded and the total spectrum or multiplex measurements derived from the spectrum are digitally processed. The excitation beam can be selected from a combination from three or more light excitation wavelengths, and multi-wavelength excitation beams including two or more wavelengths of light can be used. The exciting spectrum can be constrained by the fact that $S_e(\nu, t)$ is a positively valued function, but temporal modulation and adaptation of the exciting spectrum can effectively create bipolar or complex codes.

An array of individually laser sources that can be modulated can be used to implement a coded Raman spectrometer system. Assuming that the line width of all of the lasers is the same, ($\gamma(\nu)$), but that each source has a different center wavelength ($\nu_l$), the exciting spectrum can be expressed as follows:

$$S_e(\nu, t) = \sum_l^N f_l(t) \gamma(\nu - \nu_l) \tag{4}$$

The total source spectrum produced by this excitation can be expressed as follows:

$$S_T(\nu, t) = \tag{5}$$
$$\sum_l \left[ \int f_l(t) h_{NR}(\nu, \nu') \gamma(\nu' - \nu_l) d\nu' + \int f_l(t) h_R(\nu - \nu') \gamma(\nu' - \nu_l) d\nu' \right]$$

For relatively small shifts in the frequency of the exciting spectrum, it can be assumed that the non-Raman signal is independent of the exciting wavelength, in which case:

$$\int h_{NR}(\nu,\nu') \gamma(\nu'-\nu_l) d\nu' \approx S_{NR}(\nu) \tag{6}$$

The spectroscopy system may be used to estimate molecular densities from the Raman signal. The Raman spectrum can be estimated as follows:

$$S_R(\nu) = \int h_R(\nu-\nu') \gamma(\nu') d\nu' \tag{7}$$

In practical systems, spectral and temporal measurements may be discretely sampled. In these systems, $f_l(t)$ is a discrete function $f_{ln_t}$, designating the output power of the $l^{th}$ laser in the $n^{th}_t$ time step. In this case, Equation (5) can be written as follows:

$$S_T(\nu, n_t) = \sum_l [f_{ln_t} S_{NR}(\nu) + f_{ln_t} S_R(\nu - \nu_l)] \tag{8}$$

A model for discrete multiplex spectroscopy can be developed; however, this discussion assumes that the measurement system discretely samples the total spectrum. Another assumption is that the measurement system samples $N_\nu$ spectral lines at $N_t$ discrete times. During each time step, a coded subset of L lasers illuminates the sample being tested. Measurements include discrete vectors, m, such that $m_{n_\nu n_t} = S_T(\nu_o + n_\nu \Delta_\nu, n_t \Delta_t)$. As discussed above, a programmed set of L lasers is illuminated in each time step, such that $$m_{n_\nu n_t} = \sum_l f_{ln_t} [S_{NR}(\nu_o + n_\nu \Delta \nu) + S_R(\nu_o + n_\nu \Delta \nu - \nu_l)] \tag{9}$$

which can be expressed in matrix form as follows:

$$m = F_1 S_{NR} + F_2 S_R \tag{10}$$

where $F_1$ and $F_2$ are $N_t N_\nu \times N_\nu$ matrices such that $$F_{1(n_\nu n_t) n'_\nu} = \delta_{n_\nu n'_\nu} \sum_l f_{ln_t} \tag{11}$$

and $$F_{2(n_\nu n_t) n_\nu} = \sum_l f_{ln_t} \delta_{n_\nu \left(n'_\nu - \frac{\nu_l}{\Delta_\nu}\right)} \tag{12}$$

Equation (10) may over specify the $2N_\nu$ spectral components of $S_{NR}$ and $S_R$ in $N_1 N$ linear equations. The system designer may select $f_{ln_t}$ and $\nu_l$ to potentially improve the estimate for $S_{NR}$ on inversion of this transformation. In some embodiments, the designer can estimate one or more molecular densities without reconstructing $S_{NR}$ in its entirety.

EXAMPLE 3

Illumination Code

The total spectrum may be defined as follows:

$$S = \begin{bmatrix} S_{NR} \\ S_R \end{bmatrix} \quad (13)$$

The measurement response matrix may be defined as follows:

$$F = \begin{bmatrix} F_{11} & F_{21} \\ F_{12} & F_{22} \\ \vdots & \vdots \\ F_{1N_t} & F_{2N_t} \end{bmatrix} \quad (14)$$

Equation (10) can be expressed as follows:

$$m = FS \quad (15)$$

If it is assumed that only one spectral component is active in each illumination time step, $F_{1,nt}$ is an $N_v \times N_v$ identity matrix and $F_{2,Nt}$ is an $N_v \times N_v$ triangular matrix with one non-zero off center diagonal. For example, if $N_v = 3$ and the excitation signal consists of two exposures with the second exposure shifted from the first by one frequency bin, then $$F = \begin{bmatrix} 1 & 0 & 0 & 1 & 0 & 0 \\ 0 & 1 & 0 & 0 & 1 & 0 \\ 0 & 0 & 1 & 0 & 0 & 1 \\ 1 & 0 & 0 & 0 & 0 & 0 \\ 0 & 1 & 0 & 1 & 0 & 0 \\ 0 & 0 & 1 & 0 & 1 & 0 \end{bmatrix} \quad (16)$$

Equation (15) can be inverted to estimate S using a least squares estimator.

As an example of coded illumination Raman spectroscopy, spectra from low concentrations of dextrose in water in a quartz cuvette were obtained. Each spectrum was obtained using a single excitation wavelength. The illumination wavelengths in this example are as follows:

$$\lambda_1 = 827.03 \text{ nm} \quad (17)$$
$$\lambda_2 = 827.78 \text{ nm}$$
$$\lambda_3 = 829.33 \text{ nm}$$
$$\lambda_4 = 831.78 \text{ nm}$$

Figure 4:
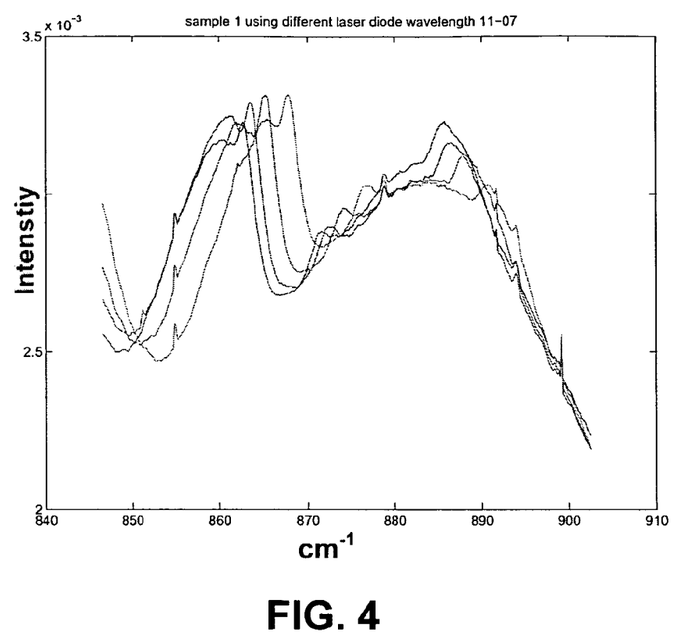
FIG. 4 is a graph illustrating Raman spectra at various excitation wavelengths for dextrose in water including fluorescence and Raman components according to embodiments of the present invention.
Figure 5:
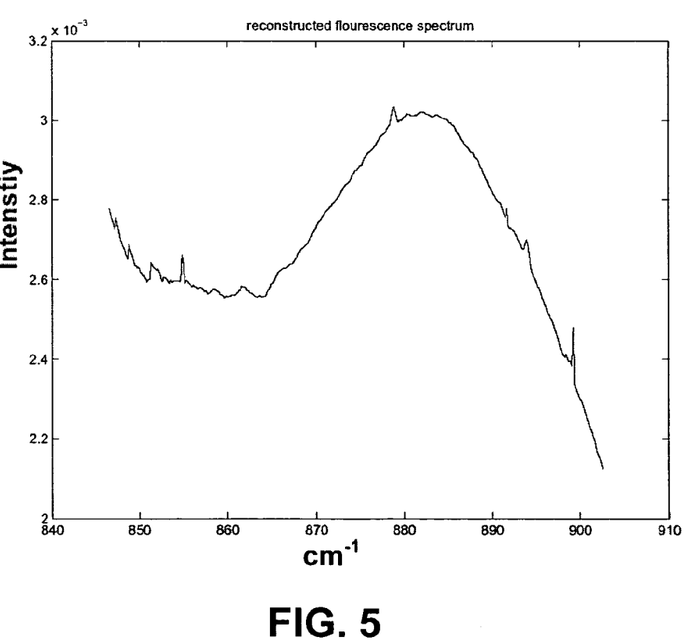
FIG. 5 is a graph illustrating the reconstructed fluorescence spectrum based on the spectra of FIG. 4.
Figure 6:
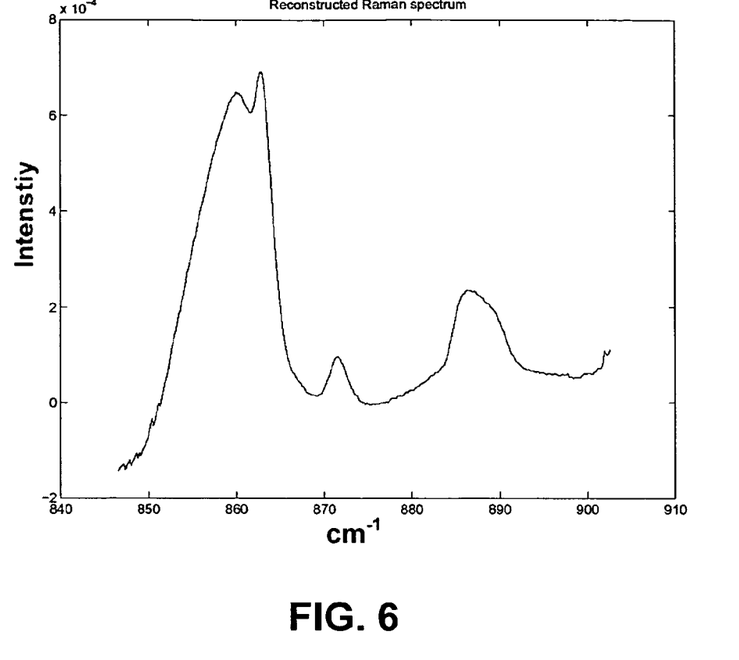
FIG. 6 is a graph illustrating the reconstructed Raman spectrum based on the spectra of FIG. 4.

The spectrum shown in FIG. 4 includes 351 sample points. Based on the number of sample points and the selected excitation wavelengths, the second Raman line should be shifted by 5 sample points from the first, the third Raman line should be shifted by 14 sample points from the first and the fourth Raman line Should be shifted by 30 sample points. Assuming this spacing, an F matrix as described above can be established and inverted using Matlab's least squares algorithm. The resulting estimated non-Raman and Raman spectra are shown in FIGS. 5 and 6 respectively.

EXAMPLE 4

MMSE (Minimum Mean Square Estimate) of Raman Spectrum

A measurement vector, <m>, can be described as follows.

$$m = Hs + N \quad (18)$$

where m has dimensions of $n \times 1$, s is the Raman spectral vector with dimensions of $p \times 1$, and N is the measurement noise vector of $n \times 1$. H is the measurement matrix of $n \times p$ satisfying $0 \leq |h_{ij}| \leq 1$. If $n \geq p$, a least squares solution to Equation (18) exists.

If the measurement matrix H is properly designed (e.g., of full column rank), the Raman spectral s can be estimated by classical least squares solution as follows:

$$\hat{s} = (H^T H)^{-1} m \quad (19)$$

It should also be pointed out that, under the WGN ("White Gaussian Noises") assumption, the classical least squares solution can be equivalent to the MLE ("Maximum Likelihood Estimate") of the linear model. The covariance matrix of the estimate in Equation (19) is as follows:

$$\text{var}(s) = E\left[(s - \hat{s})(s - \hat{s})^T\right] \quad (20)$$

$$= E\left[\{(H^T H)^{-1} H^T N\}\{(H^T H)^{-1} H^T N\}^T\right] \quad (21)$$

$$= (H^T H)^{-1} \sigma^2 \quad (22)$$

From Equation (20), the mean square error ("MSE") can be expressed as follows:

$$MSE = \frac{\sigma^2}{n} \text{trace}\left[(H^T H)^{-1}\right] \quad (23)$$

A measurement matrix H can be found, which minimizes the MSE in Equation (23), subject to the constraint that $0 \leq |h_{ij}| \leq 1$. The trivial case is when H is an identity matrix, such that MSE in Equation (23) becomes $\sigma_2$. A theoretical boundary may exist regarding how small MSE may be. The MSE can be minimized by properly designing the measurement matrix H. The derived minimum can be expressed as $\sigma^2 n$.

Since the columns of H are independent, $H^T H$ is positive and definite. Hence, $(H^T H)^{-1}$ is also positive and definite. Based on the properties of positive and definite matrices, the diagonal elements of $(H^T H)^{-1}$ are positive.

For a positive sequence, the arithmetic mean is generally greater than or equal to its geometric mean. From this, the MSE can be expressed as follows:

$$MSE = \quad (24)$$

$$\frac{\sigma^2}{n} \text{trace}\left[(H^T H)^{-1}\right] = \frac{\sigma^2}{n} \sum_{i=1}^{n} [(H^T H)^{-1}]_{ii} \geq \left(\frac{\sigma^2}{n}\right) \sqrt[n]{\prod_{i=1}^{n} [(H^T H)^{-1}]_{ii}}$$

Based on Hadamard inequality, for a positive and definite matrix, the product of its diagonal elements is greater than or equal to its determinant. Using this result, Equation 24 can be expressed as follows:

$$\prod_{i=1}^{n}\left[(H^{T}H)^{-1}\right]_{ii} \geq det\left[(H^{T}H)^{-1}\right] = [det(H^{T}H)]^{-1} \geq \left[\prod_{i=1}^{n}(H^{T}H)_{ii}\right]^{-1} \quad (25)$$

Again using the arithmetic/geometric mean inequality, Equation (25) can be expressed as follows:

$$\left[\prod_{i=1}^{n}(H^{T}H)_{ii}\right]^{-1} \geq \left[\frac{1}{n}\sum_{i=1}^{n}(H^{T}H)_{ii}\right]^{-n} = \left[\frac{1}{n}\text{trace}(H^{T}H)\right]^{-n} \quad (26)$$

By substituting Equation 25 and Equation 26 into Equation 24, the lower bound on MSE can be derived.

$$MSE \geq \frac{n\sigma^2}{\text{trace}(H^{T}H)} \quad (27)$$

where equality holds when H is orthogonal.

The quantity trace($H^T H$) is equal to the square of the Frobenious norm of H, which is essentially a measure of the total energy in the measurement matrix H. Under the constraint $0 \leq |h_{ij}| \leq 1$, trace($H^T H$) is maximized when $h_{ij} = \pm 1$.

Because equality in Equation 27 is true when H is orthogonal (such that the matrix ($H^T H$) is diagonal), and $h_{ij} = \pm 1$, the optimal solution for H is the Hadamard matrix.

When H is a Hadamard matrix, the MSE in Equation (27) achieves its theoretical minimum value, $$MSE = \frac{n\sigma^2}{\text{trace}(H^{T}H)} = \frac{n\sigma^2}{n^2} = \frac{\sigma^2}{n} \quad (28)$$

Compared With an isomorphic measurement scheme ($MSE_{Isomorphic} = \sigma^2$), the SNR improvement for Hadamard multiplexing is $$SNR_{improvement} = \frac{MSE_{Isomorphic}}{MSE_{Hadamard}} = \sqrt{\frac{\sigma^2}{\sigma^2/n}} = \sqrt{n} \quad (29)$$

The $\sqrt{n}$ improvement of SNR may be the best theoretical improvement that can be achieved. The following results can also be obtained.

1. For $0 \leq |h_{ij}| \leq 1$, the Hadamard matrix of order n minimizes Equation (23), such that $$MSE = \frac{1}{n}\sigma^2 \quad (30)$$

2. For $0 \leq h_{ij} \leq 1$, the S-matrix minimizes Equation a resulting in the following:

$$MSE = \frac{4n}{(n+1)^2}\sigma^2 \approx \frac{4}{n}\sigma^2, \quad (31)$$

For this case, the S-matrix has not been proven optimal. But the following result guarantees the suboptimality of S-matrix.

3. For $0 \leq h_{ij} \leq 1$, there exists a theoretical lower bound on MSE, which is $$MSE \geq \frac{4}{(n+1)^{\frac{n+1}{n}}}\sigma^2 \approx \frac{4}{n}\sigma^2, \quad (32)$$

See Martin Harwit, Neil J. A. Sloan, *Hadamard Transform Optics*, Academic Press, 1979.

Figure 7:
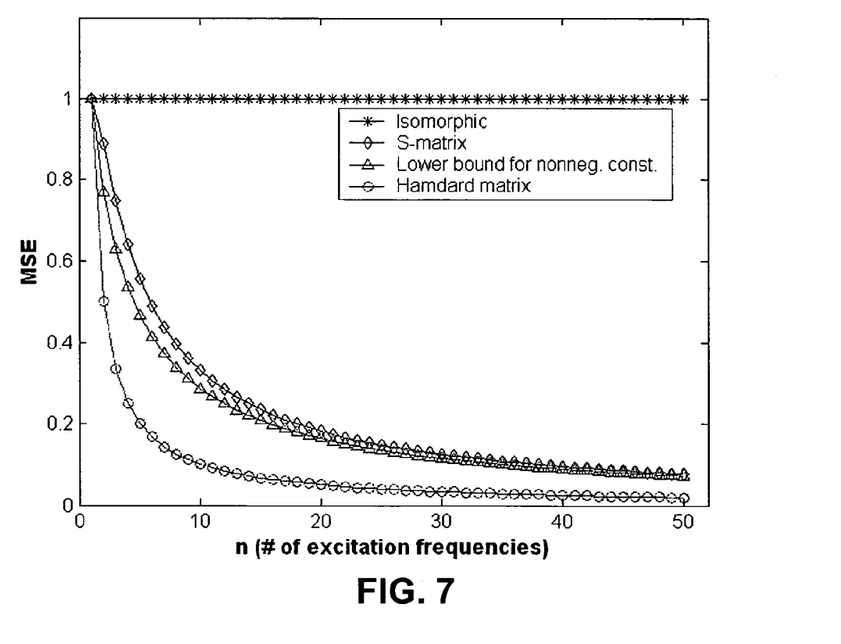
FIG. 7 is a graph illustrating the mean square error as a function of the encoding matrix size, n, for various multiplexing schemes according to embodiments of the present invention.

FIG. 7 shows the plot of MSE vs n for various multiplexing schemes. As can be seen, for all practical purposes, the S-matrix can be regarded as optimal.

EXAMPLE 5

Hadamard Spectral Temporal Illumination coding

Embodiments of the present invention provide a spectral temporal illumination scheme of multiple excitation frequencies at different time steps, and recovery of the underlying Raman spectrum without background fluorescence and with high SNR.

A Hadamard illumination scheme is used. The following is an example using 8 different excitation frequencies. The $H_{code}$ matrix is the Hadamard matrix having eight dimensions.

$$H_{code} = \begin{bmatrix} + & + & + & + & + & + & + & + \\ + & - & + & - & + & - & + & - \\ + & + & - & - & + & + & - & - \\ + & - & - & + & + & - & - & + \\ + & + & + & + & - & - & - & - \\ + & - & + & - & - & + & - & + \\ + & + & - & - & - & - & + & + \\ + & - & - & + & - & + & + & - \end{bmatrix} \quad (33)$$

Each row in the above matrix represents the coding scheme for a single time step. Assuming equal powers from all the diodes (or power normalization otherwise), the fluorescence can be reduced or eliminated by subtracting two measurements, because there are equal number of +'s and −'s for each row. To realize the coding scheme represented by a row, all the laser diodes with an element '+' in that row are illuminated together, and then those diodes with an element '−' are illuminated together. The difference between the resulting spectra can be used to provide the Raman difference spectrum.

Hadamard coding may maximize optical collection efficiency because half of the laser diodes are on for each time step, and at the same time minimize the measurement redundancy due to orthogonality of Hadamard matrix. Moreover, the Hadamard matrix is computationally efficient to invert due to its orthogonality.

The optimal excitation frequency shift may be selected to be comparable to the widths of major Raman peaks. For example, ethanol peaks have a FWHM ("full width at half maximum") of about 1.2 nm. If the resolution of the spectrometer is 0.16 nm, the effective pixel shift is on the order of 10. In all of the following simulations, the number of spectral channels is chosen to be 1000, and the pixel shift between excitation frequencies is randomly chosen between 8–12 with equal probability because the frequency shift may not be precisely controlled by tuning the temperature of the laser diode.

The Mean Squared Error ("MSE") can be used to describe the merit of reconstruction in the spectral temporal illumination system. If the measurement of noise variance is $\sigma^2$, the noise variance in the difference spectrum will be $2\sigma^2$. Assuming that the number of spectral channels is n, and the measurement matrix with Hadamard coding is H, the reconstruction MSE can be expressed as follows:

$$MSE = \frac{2\sigma^2}{n}\text{trace}[(H^T H)^{-1}] \qquad (34)$$

As can be shown in Example 7, the MSE is reduced as the number of excitation frequencies increases. The number of excitation frequencies may be limited by the following factors:

There exists (finite excitation window in which flourescence is invariant with excitation frequencies. Also, the frequency shift must also be on the order of the FWHM. Therefore, these factors may limit the largest number of allowable excitation frequencies.

More excitation frequencies may require more time to collect data, more complicated electronics and optics, and larger computational load.

Hadamard coding of the first row in Equation (33) may be challenging. Therefore, a modified Hadamard coding is proposed. The modified Hadamard matrix for four excitation frequencies is as follows:

$$H_{mod} = \begin{bmatrix} +1 & +1 & 0 & 0 \\ 0 & 0 & +1 & +1 \\ +1 & -1 & +1 & -1 \\ +1 & +1 & -1 & -1 \\ +1 & -1 & -1 & +1 \end{bmatrix} \qquad (35)$$

To study the MSE for the modified Hadamard illumination coding of dimension n, it can be shown that, $$(H_{mod}^T H_{mod})^{-1} = \frac{2}{3n^2}\begin{bmatrix} \frac{3n}{2}I_{\frac{n}{2}} + J_{\frac{n}{2}} & 2J_{\frac{n}{2}} \\ 2J_{\frac{n}{2}} & \frac{3n}{2}I_{\frac{n}{2}} + J_{\frac{n}{2}} \end{bmatrix} \qquad (36)$$

By using Equation (34), the MSE spectral reconstruction is as follows:

$$MSE_{mod} = \frac{2\sigma^2}{n}tr[(H_{mod}^T H_{mod})^{-1}] \qquad (37)$$

-continued $$= \frac{2\sigma^2}{n}\left(\frac{3n}{2} + 1\right)n\frac{2}{3n^2}$$

$$= \frac{\sigma^2}{n}\left(2 + \frac{4}{3n}\right)$$

As can be seen in Equation 37, the MSE is approximately doubled when compared to the spectral temporal coding using the original Hadamard matrix as shown in Equation (30).

To implement the first row in the modified Hadamard coding, the spectrum with all four excitation frequencies is subtracted from the spectrum with only the last two excitation frequencies. The second row can be used in the same fashion.

EXAMPLE 6

Reconstruction of Raman Spectra From Hadamard Illumination Coding

For simplicity and ease of presentation, it is assumed that the pixel shift between each excitation frequency is one. However, it should be understood that the techniques described in this example can be extended to instances in which the pixel shift is not uniform.

Assuming n pixels on a charge coupled device detector (CCD), the four shifted versions of the original Raman spectra can be represented as follows:

$$\begin{array}{ccccccccc} \lambda_1 & \lambda_2 & \lambda_3 & \lambda_4 & \lambda_5 & \lambda_6 & \lambda_7 & \lambda_8 & \cdots & \lambda_n \\ x & \lambda_1 & \lambda_2 & \lambda_3 & \lambda_4 & \lambda_5 & \lambda_6 & \lambda_7 & \cdots & \lambda_{n-1} \\ x & x & \lambda_1 & \lambda_2 & \lambda_3 & \lambda_4 & \lambda_5 & \lambda_6 & \cdots & \lambda_{n-2} \\ x & x & x & \lambda_1 & \lambda_2 & \lambda_3 & \lambda_4 & \lambda_5 & \cdots & \lambda_{n-3} \end{array} \qquad (38)$$

where each combination of excitation frequencies excites the wavelengths, $\lambda$, of one row in Equation (38). The various combinations of the rows can be measured in accordance with the encoding pattern. The notation, X, indicates the spectral channels that are outside of the expected range of the Raman spectrum, which are of limited interest. The spectral channels that are outside of the Raman spectrum range are not used in the reconstruction discussed below.

For example, considering pixel number four using the spectral temporal coding in Equation (35), the following five corresponding measurement involve $\lambda_1$–$\lambda_4$:

$$\begin{cases} m_1 = \lambda_1 + \lambda_2 \\ m_2 = \lambda_3 + \lambda_4 \\ m_3 = \lambda_1 - \lambda_2 + \lambda_3 - \lambda_4 \\ m_4 = \lambda_1 + \lambda_2 - \lambda_3 - \lambda_4 \\ m_5 = \lambda_1 - \lambda_2 - \lambda_3 + \lambda_4 \end{cases} \qquad (39)$$

Using the least squares method, the estimated spectral $\lambda_1$–$\lambda_4$ can be found. Similarly, $\lambda_2$–$\lambda_5$ can be recovered from the measurement of pixel number five. For each iteration, four spectral channels are reconstructed. If the results are arranged vertically, four shifted versions of the reconstructed Raman spectra can be shown as follows:

$$\begin{matrix} \hat{\lambda}_1 & \hat{\lambda}_2 & \hat{\lambda}_3 & \hat{\lambda}_4 & \hat{\lambda}_5 & \cdots & \hat{\lambda}_{n-3} \\ \hat{\lambda}_2 & \hat{\lambda}_3 & \hat{\lambda}_4 & \hat{\lambda}_5 & \hat{\lambda}_6 & \cdots & \hat{\lambda}_{n-2} \\ \hat{\lambda}_3 & \hat{\lambda}_4 & \hat{\lambda}_5 & \hat{\lambda}_6 & \hat{\lambda}_7 & \cdots & \hat{\lambda}_{n-1} \\ \hat{\lambda}_4 & \hat{\lambda}_5 & \hat{\lambda}_6 & \hat{\lambda}_7 & \hat{\lambda}_8 & \cdots & \hat{\lambda}_n \end{matrix} \quad (40)$$

The four reconstructed spectra in Equation (40) can be aligned and averaged to provide a final estimate of the Raman spectra.

EXAMPLE 7

Illumination Code Simulations

Figure 8:
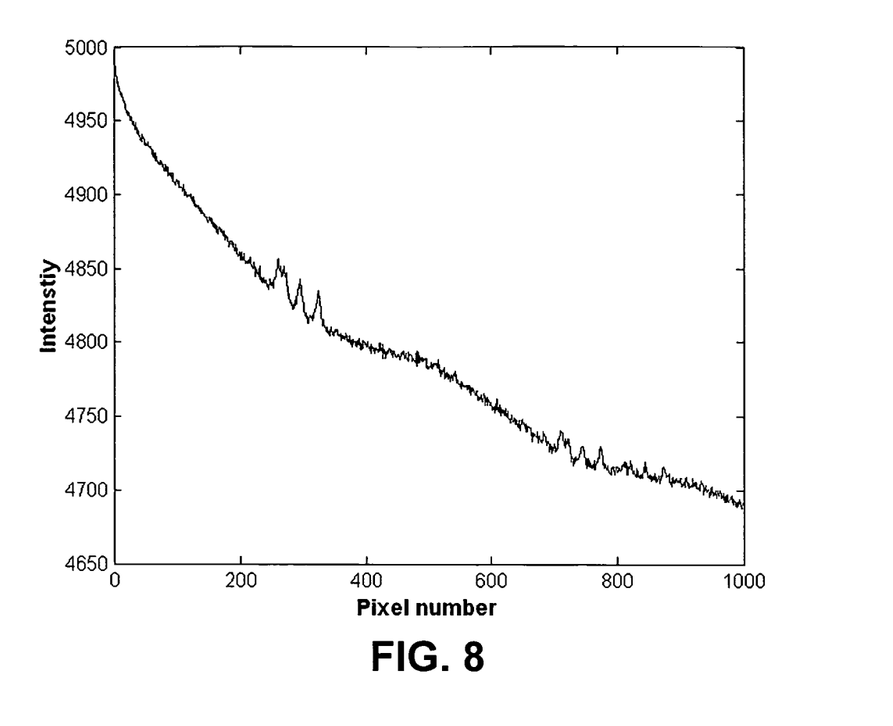
FIG. 8 is a graph of a typical simulated Raman spectrum including Raman and non-Raman components using eight excitation frequencies according to embodiments of the present invention.

FIG. 8 shows a typical measurement with a total of eight excitation frequencies. As seen in FIG. 8, the Raman spectrum is obscured by fluorescence and measurement noises.

Figure 9:
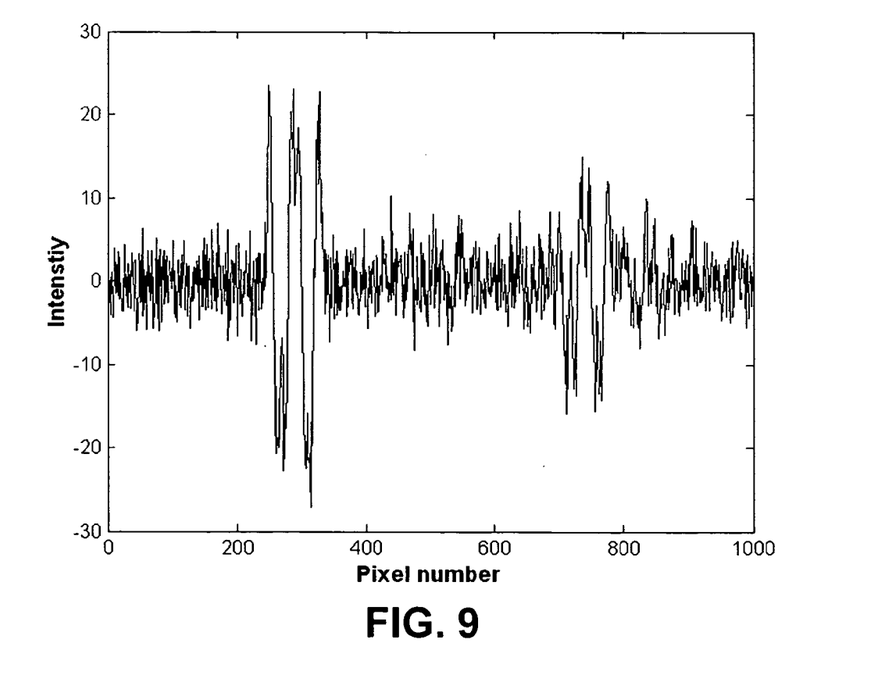
FIG. 9 is a graph of a typical Raman difference spectrum using eight excitation frequencies according to embodiments of the present invention.
Figure 10:
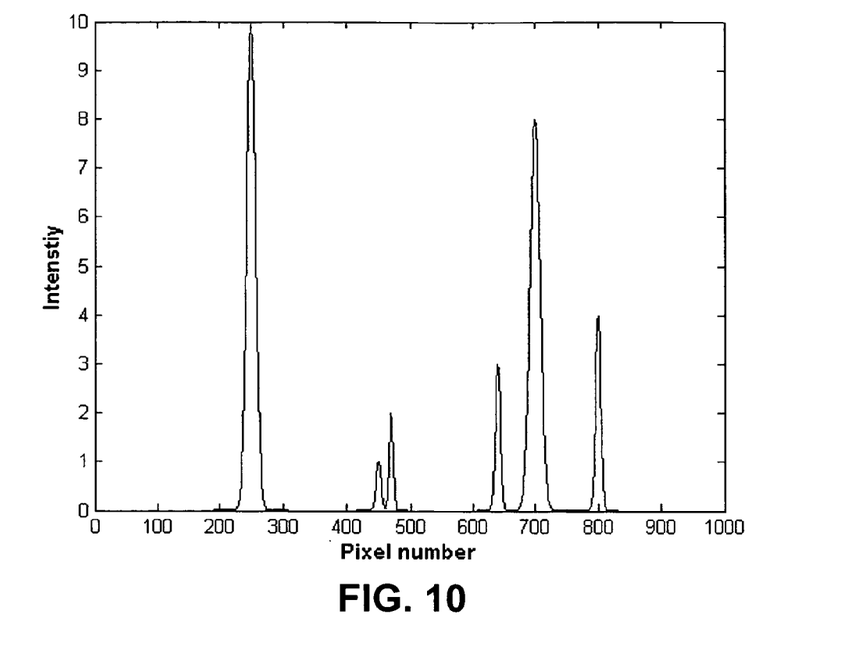
FIG. 10 is a calculated Raman spectrum.
Figure 11:
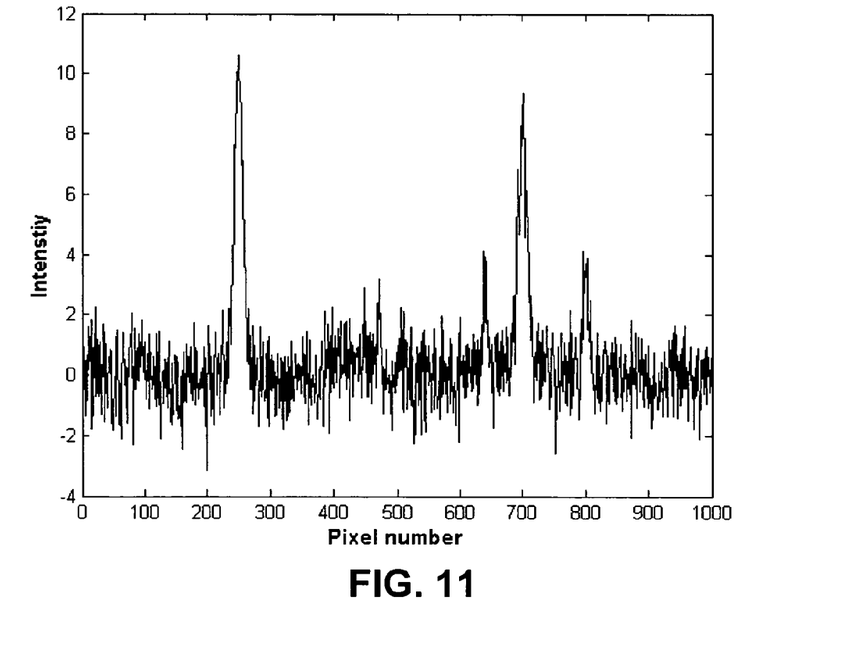
FIG. 11 is a reconstructed prior art SERDS spectrum.

FIG. 9 shows a typical Raman difference spectrum from eight excitation frequencies, which is obtained by subtracting two measured spectra. FIG. 10 is the calculated Raman spectrum, and FIG. 11 is a reconstructed Raman spectrum using SERDS.

Figure 12:
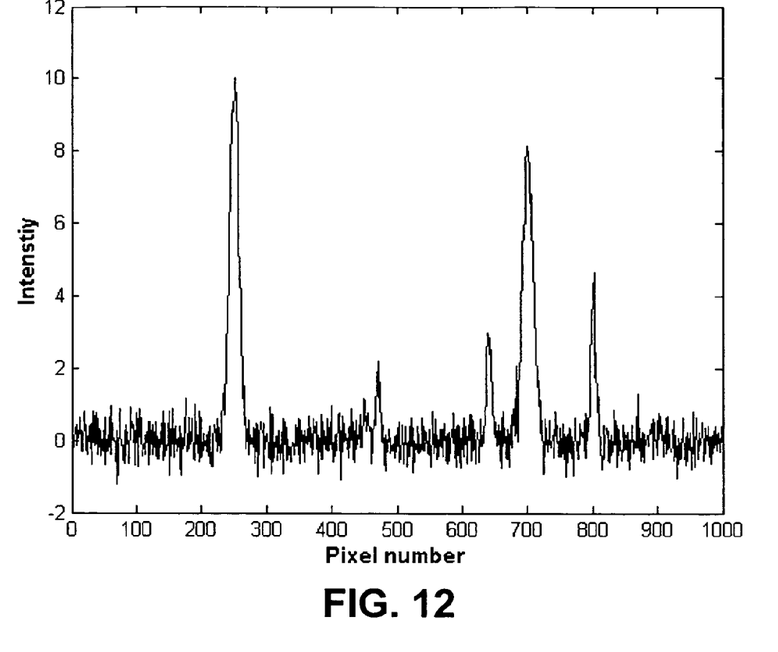
FIG. 12 is a reconstruction of a Raman difference spectrum using four excitation frequencies to reduce non-Raman components of the spectrum according to embodiments of the present invention.
Figure 13:
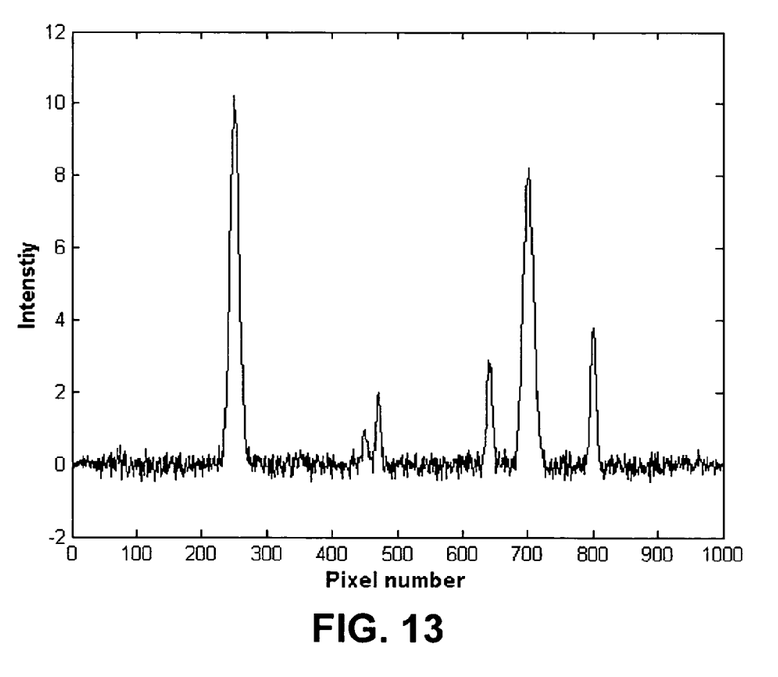
FIG. 13 is a reconstruction of a Raman difference spectrum using eight excitation frequencies to reduce non-Raman components of the spectrum according to embodiments of the present invention.
Figure 14:
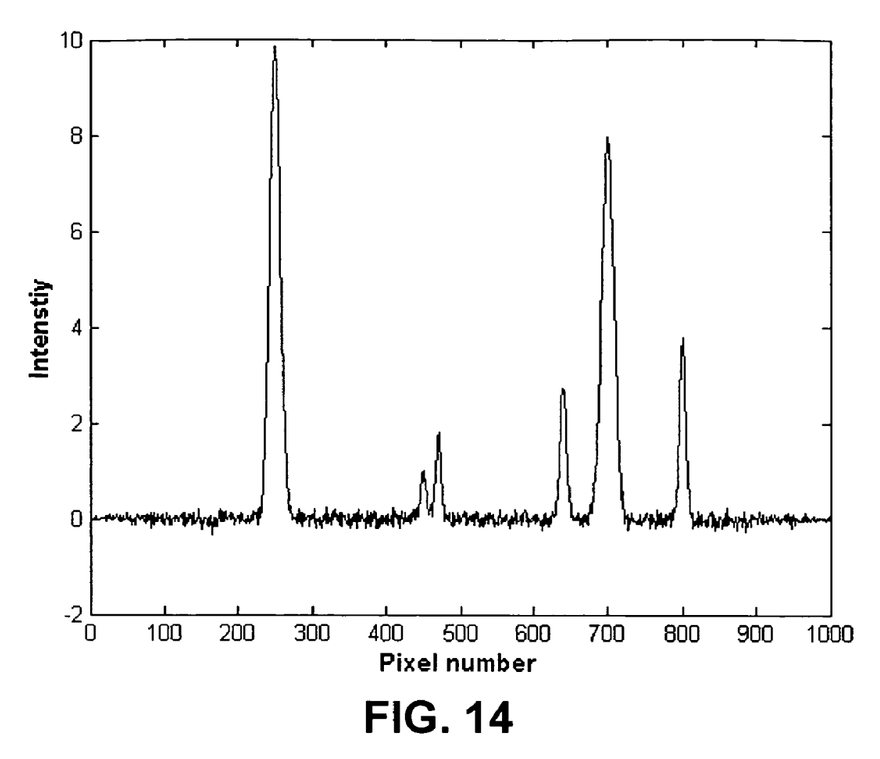
FIG. 14 is a reconstruction of a Raman difference spectrum using sixteen excitation frequencies to reduce non-Raman components of the spectrum according to embodiments of the present invention.

FIGS. 12–14 are the reconstruction results using Hadamard spectral temporal coding schemes, with 4, 8, and 16 excitation frequencies, respectively. As shown in FIGS. 12–14, as the number of excitation frequencies increases, the reconstruction SNR also improves.

The use of 16 excitation frequencies may provide sufficient SNR and reduce computational and engineering complexities.

Although embodiments of the present invention are described herein with respect to Hadamard encoding patterns, it should be understood that other encoding patterns may be used, including Walsh encoding patterns.

In the drawings and specification, there have been disclosed typical preferred embodiments of the invention and, although specific terms are employed, they are used in a generic and descriptive sense only and not for purposes of limitation, the scope of the invention being set forth in the following claims. Moreover, laser and detection configurations and techniques known to those of skill in the art may be used to accomplish the functions and features of the embodiments described herein.

What is claimed is:

1. A method for performing Raman spectroscopy comprising:
   serially impinging selected combinations from three or more light excitation wavelengths on a sample based on an encoding pattern;
   detecting a plurality of spectra from the sample responsive to the selected combinations of light excitation wavelengths; and
   identifying a shifted Raman excitation spectral component and a non-shifted spectral component characteristic of the sample based on the plurality of spectra.

2. The method of claim 1, wherein the selected combinations comprise multi-wavelength light excitation beams.

3. The method of claim 1, wherein identifying a shifted Raman excitation spectral component and a non-shifted spectral component comprises comparing ones of the plurality of spectra and identifying components of the spectra that are shifted or non-shifted responsive to changes in wavelengths of the selected combinations.

4. The method of claim 1, wherein the encoding pattern includes at least a portion of a Hadamard encoding pattern.

5. The method of claim 1, wherein the encoding pattern includes at least a portion of a Walsh encoding pattern.

6. The method of claim 1, wherein selectively impinging selected combinations from three or more light excitation wavelengths comprises selectively illuminating radiation source elements in an array of radiation source elements according to the encoding pattern.

7. The method of claim 6, wherein selectively impinging selected combinations from three or more light excitation wavelengths comprises identifying a first subset and a second subset of non-overlapping radiation source elements from the array of radiation source elements and wherein the selected combinations comprise a first excitation beam including the first subset of radiation source elements and a second excitation beam including the second subset of radiation source elements.

8. The method of claim 7, wherein identifying a shifted Raman excitation spectral component and a non-shifted spectral component comprises determining a difference between a spectrum responsive to the first excitation beam and a spectrum responsive to the second excitation beam.

9. The method of claim 7, wherein the first subset and the second subset of radiation source elements include the same number of radiation source elements.

10. The method of claim 7, further comprising selecting the first subset and the second subset of radiation source elements based on at least a portion of a Hadamard encoding pattern.

11. The method of claim 7, wherein the first subset of radiation source elements is based on a row or column of a Hadamard matrix and the second subset of radiation source elements is based on an inverse of the row or column of the Hadamard matrix.

12. The method of claim 7, wherein identifying a shifted Raman excitation spectral component and a non-shifted spectral component comprises analyzing the plurality of spectra using a Hadamard encoding pattern.

13. The method of claim 1, wherein the non-shifted spectral component comprises fluorescence radiation.

14. The method of claim 6, wherein the radiation source elements comprise laser emitting diodes or lasers.

15. The method of claim 2, wherein the multi-wavelength light excitation beams include three or more wavelengths.

16. The method of claim 1, wherein serially impinging selected combinations from three or more light excitation wavelengths comprises filtering a broadband excitation source to provide the selected wavelength combination.

17. A system for performing Raman spectroscopy comprising:
   an electromagnetic radiation source configured to serially impinge selected combinations from three or more light excitation wavelengths on a sample based on an encoding pattern;
   a detector configured to detect a plurality of spectra from the sample responsive to respective ones of the selected combinations; and
   a signal analyzer in communication with the detector configured to receive the plurality of spectra and to identify a shifted Raman excitation spectral component and a non-shifted spectral component characteristic of the sample based on the plurality of spectra.

18. The system of claim 17, wherein the selected combinations comprise multi-wavelength light excitation beams.

19. The system of claim 17, wherein the signal analyzer is configured to identify a shifted Raman excitation spectral component and a non-shifted spectral component by comparing ones of the plurality of spectra and identifying components of the spectra that are shifted or non-shifted responsive to changes in wavelengths of the selected combinations.

20. The system of claim 17, wherein the electromagnetic radiation source is configured to serially impinge the selected combinations of wavelengths based on an encoding pattern that includes at least a portion of a Hadamard encoding pattern.

21. The system of claim 17, wherein the electromagnetic radiation source is configured to serially impinge the selected combinations of wavelengths based on an encoding pattern that includes at least a portion of a Walsh encoding pattern.

22. The system of claim 17, wherein the electromagnetic radiation source comprises an array of radiation source elements and is configured to selectively impinge selected combinations from three or more light excitation wavelengths by selectively illuminating radiation source elements in the array of radiation source elements according to the encoding pattern.

23. The system of claim 22, wherein the electromagnetic radiation source is configured to selectively impinge selected combinations from three or more light excitation wavelengths by identifying a first subset and a second subset of non-overlapping radiation source elements from the array of radiation source elements and wherein the selected combinations comprise a first excitation beam including the first subset of radiation source elements and a second excitation beam including the second subset of radiation source elements.

24. The system of claim 23, wherein identifying a shifted Raman excitation spectral component and a non-shifted spectral component comprises determining a difference between a spectrum responsive to the first excitation beam and a spectrum responsive to the second excitation beam.

25. The system of claim 23, wherein the first subset and the second subset of radiation source elements include the same number of radiation source elements.

26. The system of claim 23, wherein the electromagnetic radiation source is further configured to select the first subset and the second subset of radiation source elements based on at least a portion of a Hadamard encoding pattern.

27. The system of claim 23, the first subset of radiation source elements is based on a row or column of a Hadamard matrix and the second subset of radiation source elements is based on an inverse of the row or column of the Hadamard matrix.

28. The system of claim 23, wherein the signal analyzer is configured to identify a shifted Raman excitation spectral component and a non-shifted spectral component by analyzing the plurality of spectra using a Hadamard encoding pattern.

29. The system of claim 17, wherein the non-shifted spectral component comprises fluorescence radiation.

30. The system of claim 22, wherein the radiation source elements comprise diodes or lasers.

31. The system of claim 18, wherein the multi-wavelength light excitation beams include three or more wavelengths.

* * * * *